United States Patent [19]

Harada et al.

[11] Patent Number: 5,201,901
[45] Date of Patent: Apr. 13, 1993

[54] EXPANSION UNIT AND APPARATUS FOR EXPANDING TUBULAR ORGAN LUMEN

[75] Inventors: Fumiaki Harada; Toshinobu Ishida, both of Fuji, Japan

[73] Assignee: Terumo Kabushiki Kaisha, Tokyo, Japan

[21] Appl. No.: 477,843

[22] PCT Filed: Oct. 7, 1988

[86] PCT No.: PCT/JP88/01029

§ 371 Date: Apr. 2, 1990

§ 102(e) Date: Apr. 2, 1990

[87] PCT Pub. No.: WO89/03197

PCT Pub. Date: Apr. 20, 1989

[30] Foreign Application Priority Data

Oct. 8, 1987 [JP] Japan .................. 62-252457
Nov. 2, 1987 [JP] Japan .................. 62-275655

[51] Int. Cl.⁵ .................. A61M 29/00; A61F 2/06
[52] U.S. Cl. .................. 606/198; 623/1; 623/2; 606/104
[58] Field of Search .......... 606/191, 192, 194, 195, 606/198; 623/1, 12

[56] References Cited

U.S. PATENT DOCUMENTS

| | | | |
|---|---|---|---|
| 3,868,956 | 3/1975 | Alfidi et al. | 606/198 |
| 3,923,065 | 12/1975 | Nozick et al. | |
| 4,503,569 | 3/1985 | Dotter | 623/1 |
| 4,512,338 | 4/1985 | Balko et al. | 606/195 |
| 4,610,674 | 9/1986 | Suzuki et al. | 604/282 |
| 4,665,918 | 5/1987 | Garza et al. | 623/12 |
| 4,681,110 | 7/1987 | Wiktor | |
| 4,795,458 | 1/1989 | Regan | 606/194 |

FOREIGN PATENT DOCUMENTS

| | | |
|---|---|---|
| 2248303 | 5/1975 | France . |
| 60-55964 | 4/1985 | Japan . |
| 61-6655 | 2/1986 | Japan . |
| 62-82975 | 4/1987 | Japan . |
| 62-82976 | 4/1987 | Japan . |
| 1491202 | 11/1977 | United Kingdom . |

Primary Examiner—Michael H. Thaler
Assistant Examiner—William W. Lewis
Attorney, Agent, or Firm—Frishauf, Holtz, Goodman & Woodward

[57] ABSTRACT

A tubular-organ expansion unit has a cylindrical body made of a shape memory alloy which is capable of maintaining the inside diameter of a tubular body organ. The tubular-organ expansion unit includes an X-ray contrast enhancer for improving the X-ray contrast of the tubular-organ expansion unit relative to the X-ray contrast of the tubular-organ expansion unit before the X-ray enhancer was provided on the expansion unit. In a tubular-organ expansion apparatus and a method for indwelling the tubular-organ expansion unit into a lumen of a tubular body organ, the shape memory alloy of the tubular-organ expansion unit will change its radial dimension in response to changes in temperature. The shape memory alloy may be bidirectional. The tubular-organ expansion apparatus not only includes the tubular-organ expansion unit but also comprises a catheter to which the tubular-body organ expansion unit is attached and a catheter sheath which can sheath the tubular body expansion unit and the portion of the catheter to which said unit is attached.

30 Claims, 7 Drawing Sheets

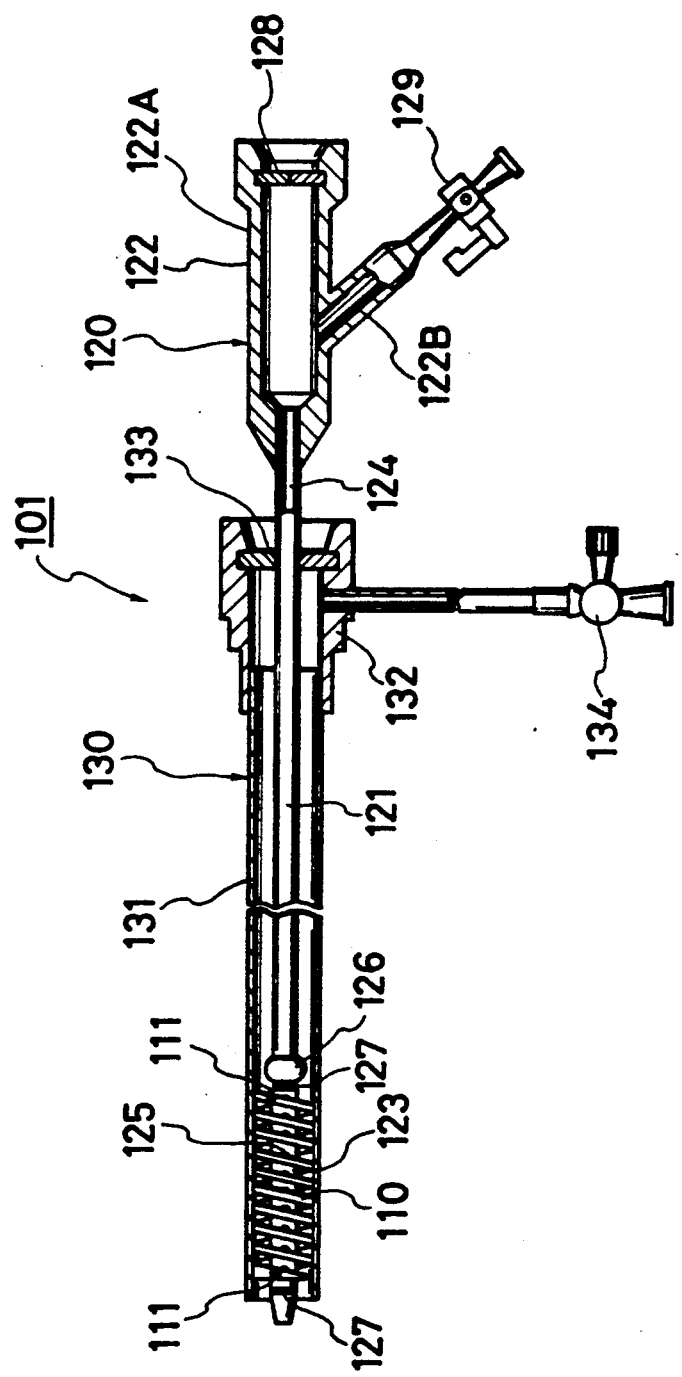

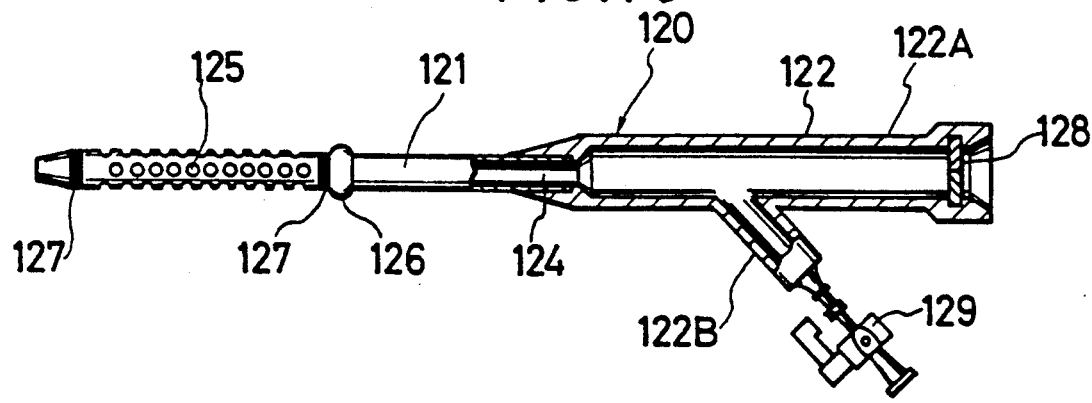
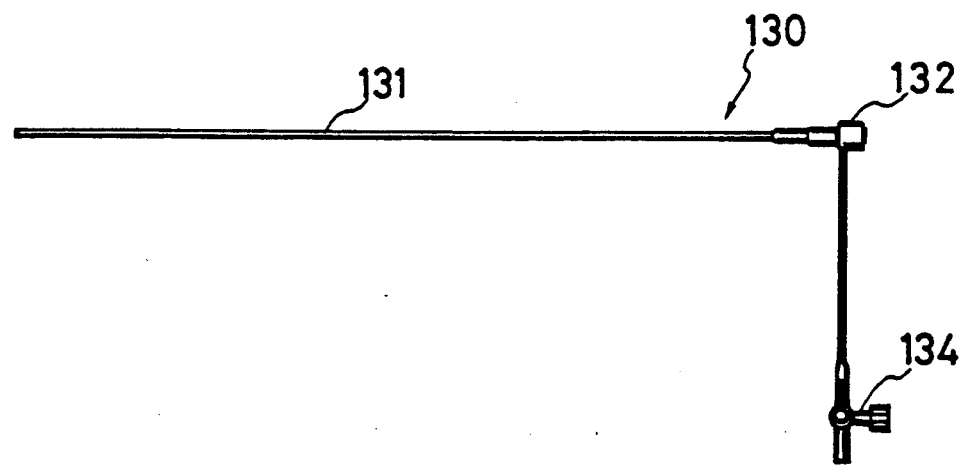

EXPANSION UNIT AND APPARATUS FOR EXPANDING TUBULAR ORGAN LUMEN

FIELD OF THE INVENTION

The present invention relates to an expansion unit for expanding the lumen of tubular organs, such as for example, a blood vessel, a digestive tube, an air tube, etc., and an apparatus for indwelling and withdrawing the expansion unit.

BACKGROUND ART

Conventionally, expansion units (stents) have been proposed to maintain the inside diameter of the luman of a tubular organ so as to prevent, for example, a coronary artery from relapsing into a constricted state after it has been dilated and indwelt by an angiectasia catheter.

A conventional expansion unit, as disclosed in Japanease Patent Examined Publication No. 61-6655, uses a unidirectional shape memory alloy made of Ti-Ni binary alloys. A tube, previously having almost the same inside measurement as that of a normal blood vessel, is shaped before its shape is memorized in the shape memory alloy. After the outside diameter of the shape memory alloy is reduced for easy introduction into a desired location of a blood vessel, the alloy is heated in warm water and the like to be expanded and recovered so as to return to the memorized shape.

(A) For example, in the work of indwelling the above-described conventional expansion unit into a desired location of the blood vessel, the expansion unit is attached to the distal end portion of a catheter and inserted to the desired location in a blood vessel using an X-ray transmission. It is therefore desirable to provide high contrast for X-rays when inserting and indwelling the expansion unit in the desired location of tubular organs, such as a blood vessel.

However, the expansion unit is thinly built because of its inherent functions, such as maintaining the inside diameter of a blood vessel after being indwelt in the blood vessel to keep a stable blood flow. For which reason, poor contrast is provided for the unit.

Further, it is difficult to say from the viewpoint of material that a shape memory alloy, for instance, Ti-Ni binary alloy, comprising the expansion unit provides high contrast.

(B) Also, in the work of indwelling the above-described conventional expansion unit made of the unidirectional shape memory alloy into a desired location in a blood vessel, as a normal practice, a guiding catheter is first dwelt in the vessel and then the expansion unit slided toward a desired location, while simultaneously passing through the inside of the guiding catheter. In this case, however, since the expansion unit slided through the narrow inside of the guiding catheter without a protective wrap around it, problems exist in that the expansion unit may get caught or deformed midway through. Furthermore, because the guiding catheter is generally very rigid, it cannot travel through a bend in the periphery in the blood vessel. Therefore, when a desired location for indwelling is farther away from the bend, the expansion unit may get caught and deformed midway through because the unit, without a protective wrap around it, together with the catheter, slides inside the vessel.

The expansion unit, which has already been proposed by the inventors of this invention, made of bidirectional shape memory alloy, is epoch-making as an expansion unit capable of changing indwelling positions and withdrawal. That is, the expansion unit is characterized in that a bidirectional shape memory alloy, in which two reversible memory shapes, high and low temperature sides, appear reversibly on the borderline of a certain transformation point, is expanded diametrically to obtain the inside measurement of a blood vessel and the like at around body temperature, and is capable of travelling inside of the blood vessel by being contracted diametrically at or below body temperature. However, the above-described expansion unit slides through the narrow inside of the guiding catheter without a protective wrap around it. As a result, such problem exists in that the expansion unit may get caught and deformed midway through. Moreover, while the expansion unit slides inside of the guiding catheter, a large amount of cooling water must be fed to keep the expansion unit contracted diametrically. Further, as is the same with a unidirectional shape memory alloy, the guiding catheter is too rigid to travel through a bend of the periphery in a blood vessel. Therefore, when the expansion unit is inserted after the guiding catheter is removed or when a desired location for indwelling is farther away from the bend, such problems exist that the expansion unit may get caught and deformed midway turough because the unit equipped with the catheter slides through the inside of the blood vessel without a protective wrap around it, and that a large amount of cooling water must be fed to keep the expansion unit contracted diametrically.

It is therefore an object of this invention to provide an expansion unit made of a shape memory alloy, which allows high contrast for X-rays, to insert and indwell the expansion unit into a desired location of a tubular organ.

It is another object of this invention to make it possible for the expansion unit to travel smoothly and readily through the tubular organ.

DISCLOSURE OF THE INVENTION (A) The present invention is that a tubular-organ expansion unit having a cylindrical body made of a shape memory alloy and capable of maintaining the inside diameter of the lumen of a tubular organ, is characterized in that a process has been conducted on at least a part of the boby for improving X-ray contrast.

Another feature of the present invention is that the cylindrical body is coil-like.

Another feature of the present invention is that the cylindrical body is a helical shape in cross section.

Another feature of the present invention is that the cylindrical body is slit lengthwise.

Another feature of the present invention is that the cylindrical body is mesh-like.

Another feature of the present invention is that the cylindrical body is defined by thin woven-shaped wires of shape memory alloy.

Another feature of the present invention is that the process includes plating of metals of a higher density than the shape memory alloy.

Another feature of the present invention is that the process means winding or pressing metals of a higher density than the shape memory alloy.

An expansion unit made of shape memory alloy according to this invention is expanded by ① external force or ② the effect of recovery in relation to memorized a shape based on temperature differences, to obtain the inside measurement of the luman of tubular organs after being inserted under contrast of X-ray transmission into a desired location in tubular organs such as a blood vessel.

Thus, the expansion unit provides high contrast for X-rays by plating or pressing at least part of the cylindrical body of the expansion unit with metals whose density is higher than that of the shape memory alloys. Accordingly, the expansion unit inserted into a tubular organ provides contrast for X-rays and is inserted and indwelt in the desired location of the tubular organ.

As regards the shape memory alloy used for the expansion unit according to this invention, for example, Ti-Ni binary alloy (composition: Ni atomic percent 50-53, preferably, 50-51, reverse transformation starting point: 30°-45° C.) is preferable.

Also, in this invention, such metals as Cu, Ag, Pt and Au whose density is higher than that of the shape memory alloy used for increasing X-rays contrast are preferable.

(B) The present invention is that the tubular-organ expansion apparatus for indwelling the tubular-organ expansion unit in the lumen of a tubular organ, is characterized in that the unit has a substantially tubular body made of a shape memory alloy and capable of changing its radial dimension in response to a change in temperature, the apparatus comprises a catheter, where the tubular-organ expansion unit can be attached to the periphery of a unit-attaching portion in the vicinity of the distal end portion of the catheter, and a catheter sheath, with both ends thereof opened, into which the attached catheter with the tubular-organ expansion unit, can be sheathed.

Another feature of the present invention is that the catheter is provided with a passageway extending from the base portion thereof to at least a location in the vicinity of the distal end portion thereof, and side pores or slit-like communication apertures on the unit-attaching portion in the vicinity of the distal end portion thereof for providing communication between the passageway and the outside of the catheter.

Another feature of the present invention is that the outside diameter of the base portion and the distal end portion of the catheter, or the outside diameter of the base of the catheter, are larger than that of the tubular-organ expansion unit attached to the unit-attaching portion.

Another feature of the present invention is that the catheter is provided with the lumen of the catheter extending from the base portion thereof to at least a location in the vicinity of the distal end portion thereof, and a hollow hub on the base portion for communicating with the lumen of the catheter, the passageway being defined by the lumen of the catheter and the lumen of the hub.

Another feature of the present invention is that the hub comprises a branch hub having two ports and one of the ports being provide with a check valve.

Another feature of the present invention is that the catheter is provided with at least one X-ray non-transmission marker in the vicinity of the distal portion thereof.

Another feature of the present invention is that an X-ray non-transmission material is mixed in the material of the catheter sheath, or the catheter sheath is provided with at least one X-ray non-transmission marker in the vicinity of the distal end portion thereof.

Another feature of the present invention is that the catheter sheath is constructed with the lumen of the sheath extending to both distal end portions thereof and a hollow hub, having a check valve, at the base thereof for communicating with the lumen of the sheath.

The present invention is that the tubular-organ expansion apparatus for indwelling a tubular-organ expansion unit in the lumen of a tubular organ, is characterized in that the unit has a substantially tubular body made of a shape memory alloy and capable of changing its radial dimension in response to a change in temperature, the apparatus comprises a catheter, whereby the tubular-organ expansion unit can be attached to the periphery of a unit-attaching portion in the vicinity of the distal end portion of the catheter, and a catheter sheath, whose inside diameter is equal to or smaller than the outside diameter of the tubular-organ expansion unit, whereby with both ends of the catheter sheath opened, the attached contracted tubular-organ expansion unit, can be sheathed.

Another feature of the present invention is that the catheter is provided with a passageway extending from the base portion thereof to at least a location in the vicinity of the distal end portion thereof, and side pores or slit-like communication apertures on the unit-attaching portion in the vicinity of the distal end portion thereof for providing communication between the passageway and the outside of the catheter.

Another feature of the present invention is that the catheter has the same outside diameter as the unit-attaching portion in the vicinity of the distal end portion thereof, which is equal to or slightly larger than the inside diameter of the tubular-organ expansion unit when the unit is contracted, and is capable of attaching the tubular-organ expansion unit to itself at substantially below body temperature.

Another feature of the present invention is that the catheter is provided with the lumen of the catheter extending from the base portion thereof to at least a location in the vicinity of the distal end portion thereof, and a hollow hub on the base portion for communicating with the lumen of the catheter, the passageway being defined by the lumen of the catheter and the lumen of the hub.

Another feature of the present invention is that the hub comprises a branch hub having two ports and one of the ports being provide with a check valve.

Another feature of the present invention is that the outside diameter of the base portion and the distal end portion of the catheter, or the outside diameter of the base portion of the catheter, are larger than that of the tubular-organ expansion unit attached to the unit-attaching portion.

Another feature of the present invention is that the catheter is provided with at least one X-ray non-transmission marker in the vicinity of the distal end portion thereof.

Another feature of the present invention is that an X-ray non-transmission material is mixed in the material of the catheter sheath, or the catheter sheath is provided with at least one X-ray non-transmission marker in the vicinity of the distal end portion thereof.

Another feature of the present invention is that the catheter sheath is constructed with the lumen of the sheath extending to both distal end portions thereof and a hollow hub, having a check valve, at the base portion thereof for communicating with the lumen of the sheath.

(A system in which the expansion unit is made of a unidirectional shape memory alloy)

In the present invention, when the expansion unit is shaped by a unidirectional shape memory alloy, a substantially coil-like or mesh-like cylindrical expansion unit, having an outside diameter almost equal to or longer than the inside diameter of a tubular organ for the unit to be indwelt, which is memorized at around body temperature, is utilized.

Since the expansion unit may be deformed freely substantially below body temperature (transformation point), it is attached to the location in the vicinity of the distal end portion of a catheter, while being wound around the tip, so as to be sheathed in a catheter sheath. As described above, the expansion unit is readily indwelt in the desired location of the tubular organ directly or with the aid of the guiding catheter by means of the combination of the catheter and the catheter sheath into the tubular organ.

Namely, a guide wire is inserted by a known technique into the tubular organ where the expansion unit is to rest, and then, along the guide wire, the expansion unit is readily inserted into the disired location by using, directly or with the aid of the guiding catheter, the combination of the catheter and the catheter sheath into the tubular organ. At this stage, according to this invention, because of the catheter sheath, the expansion unit is not directly exposed to the guiding catheter or the tubular organ so that the unit does not get caught or deformed midway through. Furthermore, because the catheter sheath is flexible, it can easily slide, along with the expansion unit and the catheter, through the bend of a blood vessel.

The expansion unit inserted according to the above-described is projected out of the catheter sheath, with the unit attached to the catheter, before being expanded by the heat of body temperature and indwelt in the desired location of the tubular organ.

While the expansion unit made of the aforementioned unidirectional shape memory alloy is inserted, cooling water may be fed from the catheter sheath and/or the catheter and while it is indwelt, warm water may be fed from the catheter sheath and/or the catheter. In a preferred embodiment in accordance with this invention, the catheter is provided with a passageway extending from its base portion to at least the location close to its end and with a communication apertures to connect the passageway to the end surface where the expansion unit is to be attached. From the communication apertures the cooling water and the warm water are fed.

In this invention, the unidirectional shape memory alloy means an alloy where a thermal plasticity type martensite transformation is developed so that the alloy is changed to the previously memorized shaped of a matrix at the reverse transformation baginning point or over. The above alloy may also be deformed freely at or under the transformation point, and once it recovers, the memorized shape at the reverse transformation point or over, it maintains the memorized shape, even at or under the reverse transformation point, unless an external force is applied.

(A system in which the expansion unit is made of a bidirectional shape memory alloy)

In the present invention, when the expansion unit is shaped by a bidirectional shape memory alloy, a substantially coil-like or mesh-like cylindrical expansion unit, having an outside diameter, almost equal to or shorter than the lumen of a tubular organ for the unit to be indwelt, which is memorized substantially below body temperature, is utilized. In the expansion unit made of the bidirectional shape memory alloy, the outside diameter, which is substantially equal to or somewhat longer than the inside diameter of a tubular organ for the unit to be expanded and indwelt at around body temperature, is memorized. While the expansion unit is attached to the catheter, the unit is sheathed into a catheter sheath. The expansion unit is readily indwelt in and withdrawn from the desired location of the tubular organ directly or with the aid of the guiding catheter by means of the combination of the catheter and the catheter sheath into the tubular organ.

That is, a guide wire is inserted by a known technique into the tubular organ where the expansion unit is to rest, and then, along the guide wire, the expansion unit is readily inserted into the desired location of the tubular organ directly or with the aid of the guiding catheter by means of the combination of the catheter and the catheter sheath into the tubular organ. According to this invention, at this stage, because of the catheter sheath, the expansion unit, while it is being attached to the catheter, is firmly maintained in the sheath. Therefore, a large amount of cooling water is not required for winding the expansion unit around the catheter tightly so as to keep the inside diameter contracted. A patient's discomfort is thus reduced. Because of the catheter sheath, the expansion unit is not directly exposed to the guiding catheter or the tubular organ so that the unit does not get caught or deformed midway through. Furthermore, because the catheter sheath is flexible, it can easily slide, along with the expansion unit and the catheter, through the bend of a blood vessel.

The expansion unit inserted according to the above-described procedure is supplied with cooling water from the catheter sheath and/or the catheter to be wound around the catheter. Under this condition, after the unit is projected out of the catheter sheath, the supply of the cooling water is stopped. As a result, the expansion unit is heated and expanded by body temperature, and indwelt in the desired location.

Moreover, the withdrawal of the expansion unit thus indwelt in the desired location is performed according to the following procedures. The guide wire is first passed the location where the expansion unit is indwelt and along with this wire, the catheter, together with the catheter sheath, is inserted into the indwelling location. The distal end portion of the catheter is then projected out of the catheter sheath. The cooling water is fed from the catheter and/or catheter sheath for winding the expansion unit around the location where the unit is to be attached so as to contract the inside diameter of the unit. The wound expansion unit is withdrawn together with the catheter into the catheter sheath. In this case, a small amount of cooling water is sufficient. Further, once the expansion unit is pulled into the catheter sheath, it is certainly withdrawn without being caught or deformed midway through.

In a preferred embodiment in accordance with this invention, the catheter is provided with a passageway extending from its base portion to at least the location in the vicinity of the distal end portion and with communication apertures, which connect the passageway and the surface of the end where the expansion unit is to be attached. When the expansion unit, made of the above-described bidirectional shape memory alloy, is inserted or withdrawn, the cooling water may be fed from the communication apertures.

In this invention, the bidirectional shape memory alloy means the alloy where previously memorized shapes at high and low temperatures on the borderline of a certain transformation point appear reversibly according to changes in temperature.

As regards shape memory alloy used for the expansion unit according to this invention, for example, Ti-Ni binary alloy (composition: Ni atomic percent 50–53, preferably, 50–51, transformation starting point: As 30°–45° C., Ms: 10°–30° C.) is preferable.

(C) The present invention is that the method of medically treating the lumen of a tubular organ by indwelling a tubular-organ expansion unit, is defined substantially cylindrically by a shape memory alloy which changes diametrically in size in response to a change in temperature, into the lumen of the tubular organ, wherein said tubular-organ expansion unit is attached to the periphery of a unit-attaching portion arranged in the vicinity of the distal end portion of the catheter, and after the combination of the catheter with the attached tubular-organ expansion unit and the catheter sheath having both ends opened, into which the catheter is sheathed, is inserted into a desired location of the tubular organ, the catheter and the tubular-organ expansion unit are projected out of the catheter sheath and the tubular-organ expansion unit is expanded by heat of the body for indwelling into the desired location.

Another feature of the present invention is that the method of medically treating the lumen of a tubular organ by indwelling a tubular-organ expansion unit, is defined substantially cylindrically by a bidirectional shape memory alloy which changes diametrically in size in response to a change in temperature, into the lumen of the tubular organ, wherein the tubular-organ expansion unit is attached to the periphery of a unit-attaching portion arranged in the vicinity of the distal end portion of a catheter, and after the combination of the catheter with the attached tubular-organ expansion unit and the catheter sheath having both ends opened, into which the catheter is sheathed, is inserted into a desired location of the tubular organ, the catheter and the tubular-organ expansion unit are projected out of the catheter sheath and the tubular-organ expansion unit is expanded by heat of the body for indwelling into the desired location.

Another feature of the present invention is that the medical treatment method is characterized in that after the combination of the catheter and the catheter sheath is inserted into a location where the tubular-organ expansion unit is to be indwelt, the distal end portion of the catheter is projected out of the catheter sheath, the tubular-organ expansion unit then being reduced in size by the feeding of cooling water from the catheter sheath and/or the catheter in order to be wound around the unit-attaching portion of said catheter, and the wound tubular-organ expansion unit, together with the catheter, is withdrawn inside the catheter sheath.

Another feature of the present invention is that the method of medically treating the lumen of a tubular organ by indwelling a tubular-organ expansion unit, is defined substantially cylindrically by a shape memory alloy which changes diametrically in size in response to a change in temperature, into the lumen of the tubular oragan, wherein the tubular-organ expansion unit is attached to the periphery of a unit-attaching portion arranged in the vicinity of the distal end portion of a catheter, and after the combination of the catheter with the attached tubular-organ expansion unit and the catheter sheath having both ends opened, into which the catheter is sheathed, is inserted, through the lumen of a guiding catheter already indwelt in the tubular organ, into a desired location of the tubular organ, the catheter and the tubular-organ expansion unit are projected out of the catheter sheath and the tubular-organ expansion unit is expanded by heat of the body for indwelling into the desired location.

Another feature of the present invention is that the method of medically treating the lumen of a tubular organ by indwelling a tubular-organ expansion unit, is defined substantially cylindrically by a shape memory alloy which changes diametrically in size in response to a change in temperature, into the lumen of the tubular organ, wherein the tubular-organ expansion unit is attached to the periphery of a unit-attaching portion arranged in the vicinity of the distal end portion of a catheter, and after the combination of the catheter with the attached tubular-organ expansion unit and the catheter sheath having both ends opened, into which the catheter is sheathed, is inserted, through the lumen of a guiding catheter already indwelt in the tubular organ, into a desired location of the tubular organ, the catheter and the tubular-organ expansion unit are projected out of the catheter sheath and the tubular-organ expansion unit is expanded by heat of the body for indwelling into the desired location.

Another feature of the present invention is that the medical treatment method is characterized in that after the combination of the catheter and the catheter sheath is, through the lumen of a guiding catheter already indwelt in the tubular organ, inserted into a location where the tubular-organ expansion unit is to be indwelt, the distal end portion of the catheter is projected out of the catheter sheath, the tubular-organ expansion unit then being reduced in size by the feeding of cooling water from the catheter sheath and/or the catheter in order to be wound around th unit-attaching portion of the catheter, and the wound tubular-organ expansion unit, together with the catheter, is withdrawn inside the catheter sheath.

BRIEF DESCRIPTION OF THE DRAWINGS

FIG. 8 is a cross-sectional view showing an expansion system of a fifth embodiment according to this invention;

FIG. 9(A), (B) is a side view showing the expansion unit;

FIG. 10 is a side view illustrating a catheter;

FIG. 11 is a side view showing a catheter sheath;

THE BEST MODE FOR CARRYING OUT THE INVENTION

FIRST EMBODIMENT

An expansion unit 10 (hereinafter referred to as a stent) is substantially cylindrically (coil-like in this embodiment) formed by a unidirectional shape memory alloy which changes the size diametrically in accordance with changes in temperature. The measurement of the stent 10 in its matrix is set to a smaller size than that of a tubular organ, in this embodiment a blood vessel 11 (Refer to FIG. 1(A)). Also, in this embodiment, the reverse transformation starting point for the shape memory alloy comprising the stent 10 is set at a temperature above body temperature in order to change the stent 10 diametrically after the point exceeds the body temperature. The stent 10 is further expanded diametrically by an external force (Refer to FIG. 1(B)). In this invention, a unidirectional shape memory alloy means the alloy, in which a thermal plasticity type martensite transformation is developed so that the alloy is changed to the previously memorized shaped of a matrix at or over the reverse transformation beginning point. The above alloy may also be deformed freely at or under the transformation point, and once it recovers the memorized shape at or over the reverse transformation point, it maintains the memorized shape, even at or under the reverse transformation point, unless an external force is applied.

The distal end portion of the cylindrical stent 10 is a high contrast portion 10a. The high contrast portion 10a is formed by the plating or pressing metals with a higher density (for example, Cu, Ag, Pt and Au) than the shape memory alloy comprising the stent 10. The high contrast portion may be at the rear end of, or at the center of, or at any two points of the stent 10, or the whole body of the cylindrical stent 10.

Figure 2:
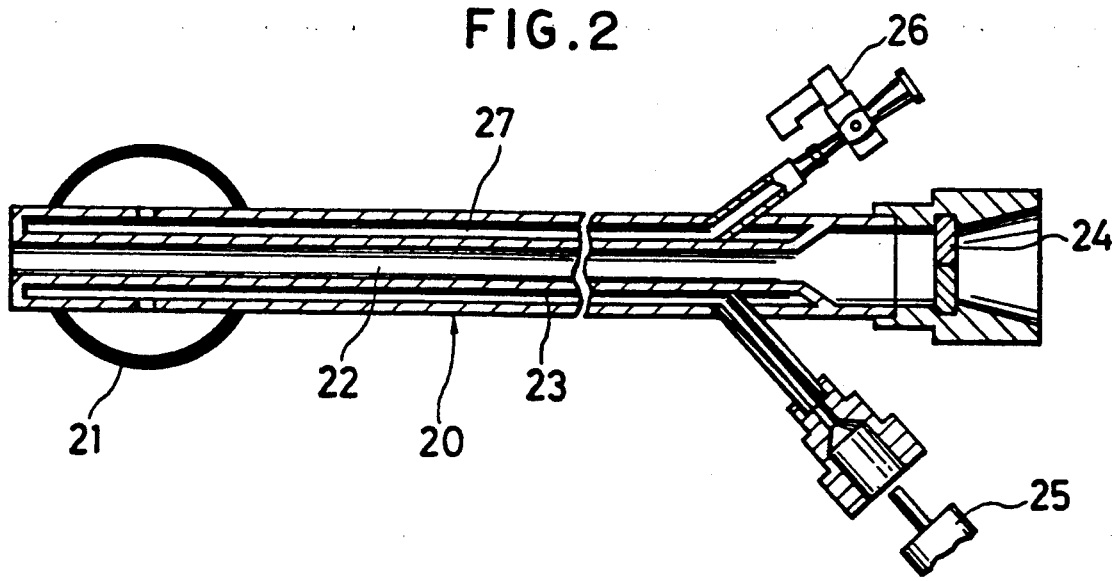
FIG. 2 is a cross-sectional view illustrating an indwelling catheter.

As shown in FIG. 2, for example, an indwelling catheter 20, is used for indwelling the above mentioned stent 10 into a desired location of a tubular organ. The indwelling catheter 20 is provided with a balloon 21 at its distal end and is guided by a guide wire (28 of FIG. 4(A), (B)), which is inserted to a main passageway 22, toward the desired location of the tubular organ. The balloon 21 is expanded by a balloon swelling liquid fed from a subpassageway for liquid injection 23 so as to provide the reduced-diameter stent 10 already attached around the balloon with an external force. A hub of the main passageway 22 is provided with a check valve 24 to prevent blood leakage and the like caused by the passing of the guide wire. Numeral 25 indicates an insufflator, and 27 an outlet subpassageway communicating with the inside space of the balloon 21. The outlet subpassageway 27 is provided with a three-way cock 26 at its base.

Figure 3:
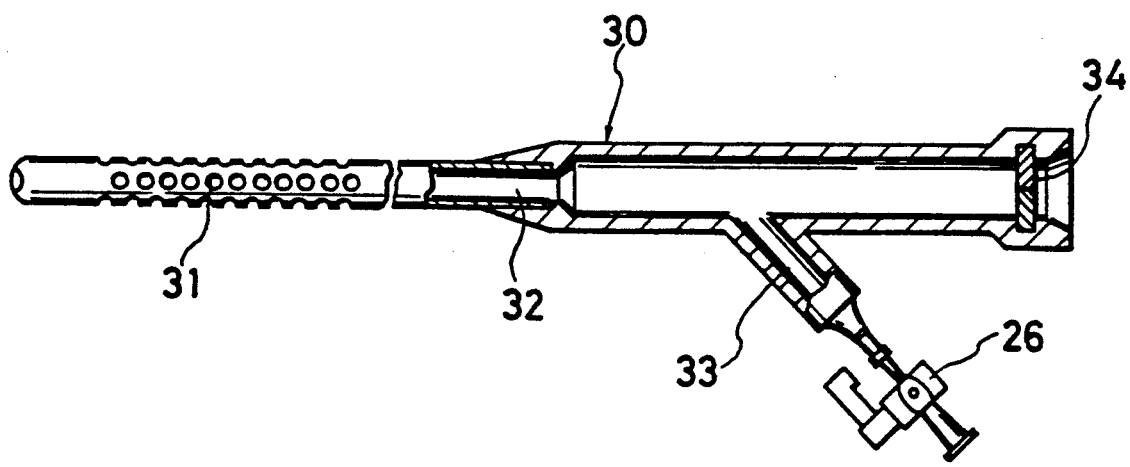
FIG. 3 is a cross-sectional view illustrating a withdrawing catheter.

Further, as shown in FIG. 3 for instance, a withdrawing catheter 30 is used for withdrawing (or changing an indwelling location) after the aforementioned stent 10 is indwelt. The withdrawing catheter 30 is provided with side pores 31 on its distal end and guided by a guide wire (37 of FIG. 4(C)) to the location in the tubular organ where the stent is to rest. A stent heating liquid, fed from a subpassageway for liquid injection 33 into a main passageway 32, flows out of the side pores 31 so at to heat the expanded stent located around the side pores 31 up to over the reverse transformation starting point or over. Consequently, the memory shape in the matrix of the stent is recovered or reduced in its size. A hub of the main passageway 32 is provided with a check valve 34 to prevent blood leakage and the like caused by the passing of the guide wire. A boss of a subpassageway 33 is provided with a three-way cock 26 to inject the stent heating liquid.

The effect of the above-described stent 10 will now be described.

Figure 4A:
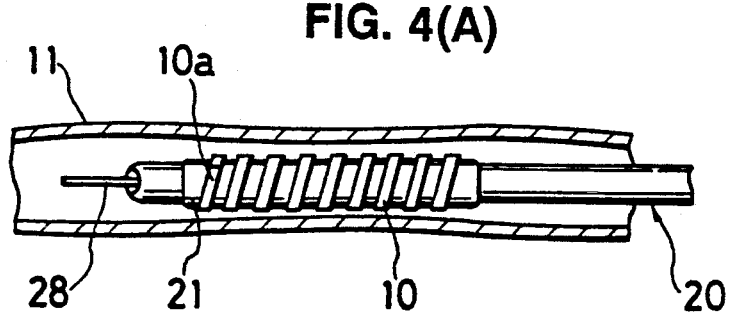
FIG. 4(A) is a schematic illustration showing the expansion unit while it is being inserted.
Figure 4B:
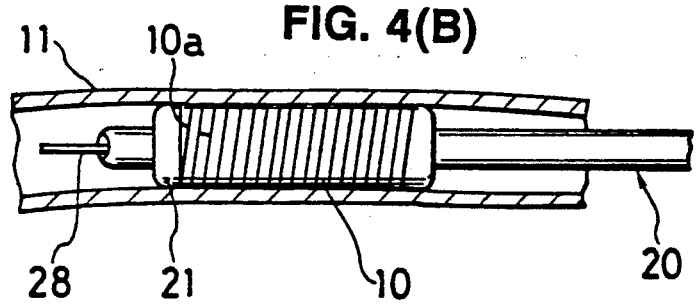
FIG. 4(B) is a schematic illustration showing the expansion unit while it is indwelt.

According to the stent 10 described above, at or under the transformation point of the shape memory allow, the stent 10 is reduced to a size smaller than the inside measurement of the blood vessel. As shown in FIG. 4(A), the balloon 21 is attached to the distal end portion of the indwelling catheter 20 and inserted into the desired location of the blood vessel 11 under an X-ray contrast, and then, as shown in FIG. 4(B), the stent 10 is expanded in size by the external force caused by the swelling of the balloon 21 so that the stent 10 is indwelt, thus obtaining the inside diameter of the blood vessel 11.

Figure 4C:
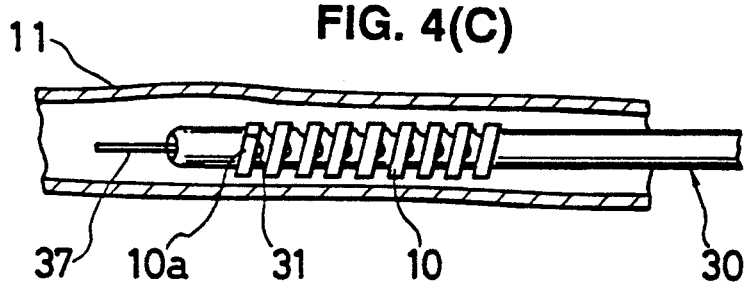
FIG. 4(C) is a schematic illustration showing the expansion unit while it is being withdrawn.

As shown in FIG. 4(C), when the stent described above is withdrawn, or when the indwelling location of the stent is changed, the withdrawing catheter 30, with the side pores 31 at its distal end portion, is inserted into the location where the stent 10 is indwelt. A liquid, having the reverse transformation starting point or over for the shape memory alloy, flows out of the side pores 31 and causes the stent 10 to exceed the reverse transformation starting point for returning to the once memorized shape or for making the diameter of the stent smaller than the inside diameter of the blood vessel 11. Thus the stent 10 can travel along with the withdrawing catheter 30, just like while being wound around the distal end portion of the withdrawing catheter 30.

That is, even after the catheter 10 is expanded in the blood vessel 11, it can be freely reduced in size. For which reason, it is possible to withdraw it from the indwelling location and change locations.

Further, the stent 10 is provided with the high contrast portion 10a formed by plating or pressing higher density metals than the shape memory alloy with at least a part of the stent 10, thereby providing high contrast. Thus, the stent 10 inserted into the inside of the blood vessel 11 definitely provides contrast under X-ray and can be indwelt into a desired location.

As regards the shape memory properties in accordance with the present invention, in addition to the properties for the stent 10 described above, other properties as follows are acceptable: a bidirectional shape memory alloy, in which two reversible memory shapes, i.e., high and low temperature sides, appear reversibly on the borderline of a certain transformation point, which is expanded diametrically to obtain the inside diameter of a blood vessel and the like at around body temperature, and which is capable of travelling inside of the blood vessel by being contracted diametrically at or below body temperature.

As regards the shape of the stent 10 according to this invention, other than the coil-like stent 10 of the first embodiment, substantially cylindrical things are included. "Substantially cylindrical things" in this invention mean things which have a surface contacting with at least part of a lumen for expanding and maintaining the lumen of a tubular organ.

SECOND EMBODIMENT

Figure 5A:
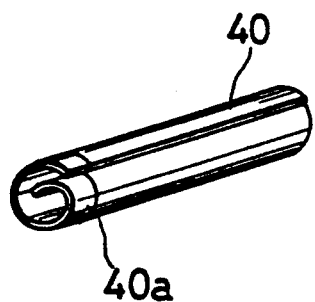
FIG. 5(A), (B) is a perspective view showing the expansion unit of a second embodiment in accordance with this invention.
Figure 5B:
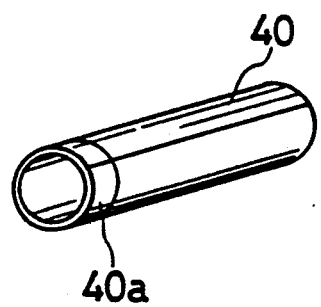

A stent 40, according to a second embodiment, is constructed in a herical shape in cross section so as to contract (FIG. 5(A)), or expand (FIG. 5(B)). Numeral 40a indicates a high contrast portion.

THIRD EMBODIMENT

Figure 6A:
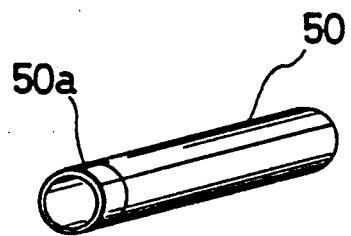
FIG. 6(A), (B) is a perspective view depicting the expansion unit of a third embodiment according to this invention.
Figure 6B:
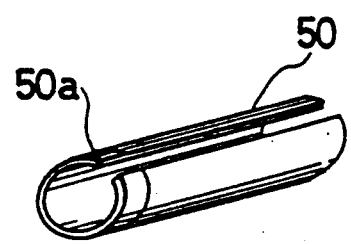
Figure 7A:
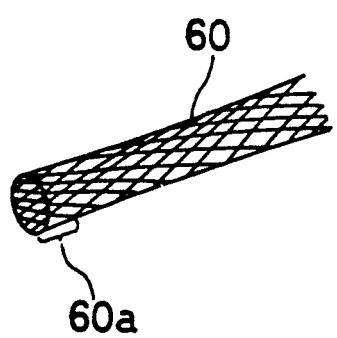
FIG. 7(A), (B) is a perspective view illustrating the expansion unit of a fourth embodiment according to this invention.
Figure 7B:
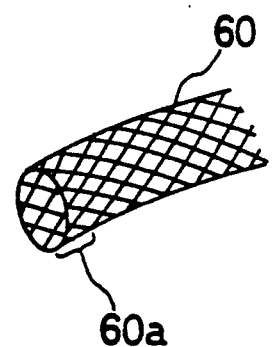

A stent 50, with a longitudinal slit, according to a third embodiment, is cylindrically constructed so as to contract (FIG. 6(A)) or expand (FIG. 6(B)). Numeral 50a indicates a high contrast portion.

FOURTH EMBODIMENT

A stent 60, according to a fourth embodiment, is constructed in a mesh-like manner so as to contract (FIG. 6 (A)), or expand (FIG. 6(B)). It is desirable that the distal end portion of the mesh be fixed by means of welding or an adhesive so that the thin wires of the shape memory alloy do not come loose. It is further desirable that the intersections comprising the thin wires of the alloy be fixed by means of welding or an adhesive. Numeral 60a indicates a high contrast portion.

The effects of the embodiments in accordance with this invention will now be specifically described.

Figure 1A:
FIG. 1(A), (B) is a side view showing an expansion unit of a first embodiment according to the present invention.
Figure 1B:
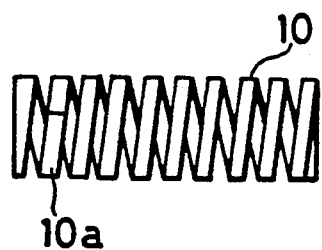

The same shape stent, as shown in FIG. 1(A), (B), made of Ti-Ni binary allow (including atomic percent approximately 51), with a wall thickness of 0.004 mm, a width of 1 mm, is washed off with water after an electrolytic degreasing and an acid treatment, and plated with Au in the solution of $KAu(CN)_2$. When the already plated stent, and another stent not yet plated, are contrasted by X-rays under the same condition, the plated stent proves to provide improved contrast.

For proof of the improvement in contrast of the Au plating, the stent with Au plating and the stent not yet plated are exposed by X-rays under the condition of 45 kV and 2.0 mA, and a contrast picture is obtained. The absorbance of 600 nm of the picture is then obtained by a Shimazu second wavelength chromato scanner made by Shimazu Corp. In the spectrum thus obtained, let the contrast of the complete transmission of X-rays be 0, and the section where plating is not yet performed 1, then the Au plated stent becomes 3. A remarkable improvement in contrast by Au plating is proved.

FIG. 8 is a cross-sectional view showing an expansion system of a fifth embodiment according to this invention;

FIG. 9(A), (B) is a side view showing the expansion unit;

FIG. 10 is a side view illustrating a catheter;

FIG. 11 is a side view showing a catheter sheath; and

FIG. 12(A) to (E) is a schematic illustration showing the expansion unit in processes of inserting and withdrawing.

FIFTH EMBODIMENT

An expansion system 101 is constructed in a combination of the expansion unit (stent) 110, the catheter 120 and the catheter sheath 130.

As shown in FIG. 9(A), (B), the stent 110 is molded substantially, in a cylindrical and spiral manner, by a thin wire of a flat bidirectional shape memory alloy (made of, for example, Ni-Ti binary, Cu-Al-Ni ternary, Cu-Zn-Al ternary). The stent 10 is kept expanded diametrically in its shape or at around body temperature (for example, 30°–35° C.) (FIG. 9(B), and is contracted diametrically in its shape substantially below body temperature (for example, 15°–25° C.) (FIG. 9(A)). In the stent (Ti-Ni binary bidirectional shape memory allow: Ni atomic percent about 51, a wall thickness of 0.03 mm, a width of 1 mm), the inside measurement thereof changes to $\phi 1.6$ mm at or under 20° C., and to $\phi 2.8$ mm at or over 32° C.

The inside diameter, length, etc. of the stent 110 may be appropriately determined by the inside diameter and the length of a tubular organ where the stent is to rest. That is, the inside diameter of the stent 110 is made equal to that of the tubular organ, such as a blood vessel, for the stent is to rest, when it is expanded, and is made small enough for the stent to be guided to a location where the stent is indwelt.

In this embodiment, the shape of the stent is not limited to the spiral shape described, but may be substantially cylindrically formed, such as for example, in a mesh-like or a herical shape.

Furthermore, it is desirable that the stent 110 be provided with an X-ray non-transmission marker 111 on at least part of the cylindrical body thereof.

The catheter 120 comprises a catheter tube 121 (made of thermoplastic resins, such as polyethylene, EVA or PVC) and a hollow hub 122 (made of, for example, polycarbonate or polyethylene) at the base of the catheter tube 121 to communicate with a lumen extending from the base of the catheter tube 121 to the distal end portion thereof. The catheter 120 allows the provision of the above-mentioned stent 110 on the periphery of a stent-attaching portion 123 close to the distal end portion of the catheter tube 121.

The catheter 120 also provides a passageway 124 between the lumen in the catheter tube 121 and the inside of the hub 122. The stent-attaching portion 123 of the catheter tube 121 is provided with a large number of side pores-like communication apertures 125 for communicating between the passageway 124 and the outside. The stent cooling water fed to the passageway 124 is discharged radiately from the communication apertures 125. The communication apertures may also be slit-like.

It is further desirable that the stent 120 be provided with an expansion 126, on the base portion of the stent-attaching portion 123 where the communication apertures 125 are located, and which has an outside measurement larger than that of the stent 110 attached to the stent-attaching portion 123. The reason for the above arrangement is that when the stent 110 is withdrawn, it is pulled inside the catheter sheath 130 while being wound around the stent-attaching portion 123. This prevents the catheter from being caught at the distal end portion of the catheter sheath 130. The expansion 126 may be arranged on both the base side and the distal end portion side of the stent attaching portion 123.

Moreover, it is desirable that the catheter 120 be provided with an X-ray non-transmission marker 127 (made of, for instance, gold or platinum) at a location in the vicinity of the distal end portion of the catheter tube 121. The marker permits confirmation of the location of the catheter 120 under x-ray fluoroscopy and the relative locations of the stent 110 and the sheath 130.

As shown in FIG. 10, the hub 122 of the catheter 120 comprises a linear cylindrical body 122A and a branch 122B branched at the center of the body 122A. The linear cylindrical body 122A serves as an entrance for the guide wire. A check valve 128 (made of a flexible material, such as silicone rubber) is arranged close to the opening of the base of the body to prevent blood leakage and the like caused by the guide wire. The branch 122B, equipped with a three-way cock 129, is utilized for introducing cooling water and the like.

The catheter sheath 130 comprises a catheter tube 121, with both distal end portions opened, (made of, for example, PVC, polyethylene and fluorocarbon resin) and a hollow sheath hub 132 (made of, for example, polycarbonate or polyethylene) at the base of a catheter tube 121 to communicate with the lumen of the sheath tube 131. The catheter 120 with the stent 110 attached may be attached on the lumen of the catheter sheath 130.

The catheter sheath 130 must be flexible to travel through any bends in the periphery of a blood vessel, with the stent 110 and the catheter 120 sheathed into it. For this purpose, as the sheath 130 may be made of polyvinyl chloride, 15-40 parts by weight, preferably 20-30 of diethylhexylphthalate (DEHP) in a plasticizer are desirably contained for 100 parts by weight of polyvinyl chloride.

The catheter sheath 130 may desirably include the catheter tube 131, in whose material an X-ray contrast medium is so mixed as to confirm the location of each component under X-ray transmission. The catheter sheath 130 may also be provided with at least one X-ray non-transmission marker in the vicinity of the distal end portion of the sheath tube 131.

It is also desirable that the inside diameter of the sheath tube 131 of the catheter sheath 130 be smaller than that of the diameter of the stent 110 when it is expanded. This is because when the stent 110 is inserted by means of a combination of the stent 110, the catheter 120 and the sheath 130, the stent 110 is fixed to the inside of the sheath 130 due to the fact that the stent 110 tends to expand to a size larger than the inside diameter of the sheath. For the above-described reason, when the stent 110 is inserted by means of the combination of the stent 110, the catheter 120 and the sheath 130, into a location close to the indwelling location, the cooling water must not flow to wind the stent 110 around the catheter 120. Thus, firm insertion of the stent is achieved. A patient's discomfort will be greatly reduced by a small amount of the cooling water required.

A sheath hub 132 of the catheter sheath 130 is provided with a check valve 133 for preventing blood from being leaked by the passing of the catheter 120 through the boss. The sheath hub 132 is further provided with a sheath port 134 for injection of a contrast medium and the like.

The effect of the above-mentioned embodiment will now be described.

The expansion system 101 hitherto described comprises the stent 110 made of the bidirectional shape memory alloy, where the outside diameter of the stent, smaller than the inside diameter of the lumen of the tubular organ within which the stent is to rest, is memorized when the temperature in the system is substantially below body temperature. Moreover, the stent 110 expands at around body temperature, and memorizes its outside diameter, equal to or somewhat larger than the inside diameter of the lumen of the tubular organ where the stent is to rest. The stent 110 is sheathed into the catheter sheath 130, while it is attached to the catheter 120. The stent 110 is readily indwelt in and withdrawn from a desired location of the tubular organ by inserting the above combination into the location.

Figure 12A:
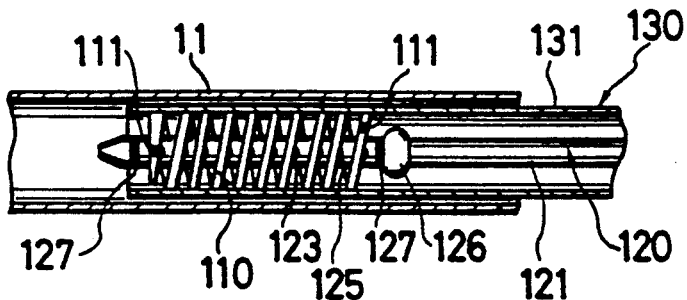
FIG. 12(A) to (E) is a schematic illustration showing the expansion unit in processes of inserting and withdrawing.

That is, a guide wire is inserted by a known technique into the tubular organ where the stent is to rest, then, along the guide wire, the stent 110 is readily inserted into the desired location by using the above combination (Refer to FIG. 12(A)).

Figure 13:
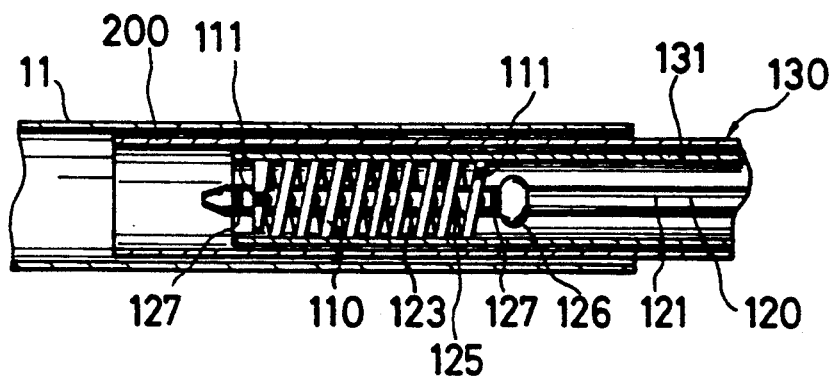
FIG. 13 is a schematic illustration showing the expansion unit in another process of inserting and withdrawing.

As shown in FIG. 12(A), instead of introducing directly a combination of the stent 110, the catheter 120 and the catheter sheath 130 into the tubular organ 11, it may be acceptable that, as shown in FIG. 13, the above combination is first introduced to the inside of the guiding catheter 200, which is already indwelt in the tubular organ 11, and then inserted into the tubular organ 11. At this stage, the guiding catheter 200 encounters the problem that it can hardly pass through a bend in the periphery of the blood vessel because of its relative stiffness. This means that it is difficult for the guiding catheter 200 to be indwelt beforehand in the desired location of the tubular organ 11. Therefore, when the desired location is farther away from the indwelling location of the guiding catheter 200, the combination of the stent 110, the catheter 120 and the catheter sheath 130 is directly inserted into the tubular organ 11, after the combination passes the end of the location where the guiding catheter is indwelt.

According to this invention, at this time, since the stent 110 is firmly maintained within the catheter 120 thanks to the catheter sheath 130, while it is attached to the catheter 120, a large amount of cooling water must not be fed to keep the stent reduced in size, as when winding the stent around the catheter 120 tightly. This will reduce the patient's discomfort. Moreover, because of the catheter sheath 130, the stent 110 is not directly exposed to the guiding catheter 200 or the tubular organ 11, and is prevented from being caught or deformed midway through.

Figure 12B:
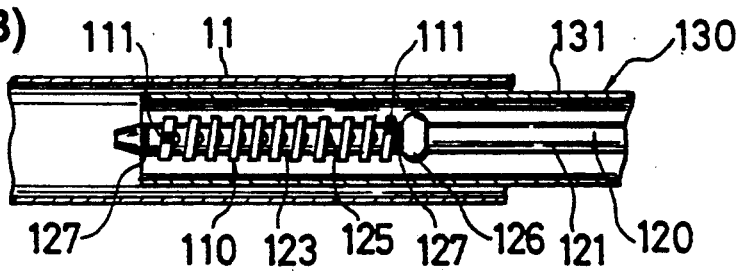
Figure 12C:
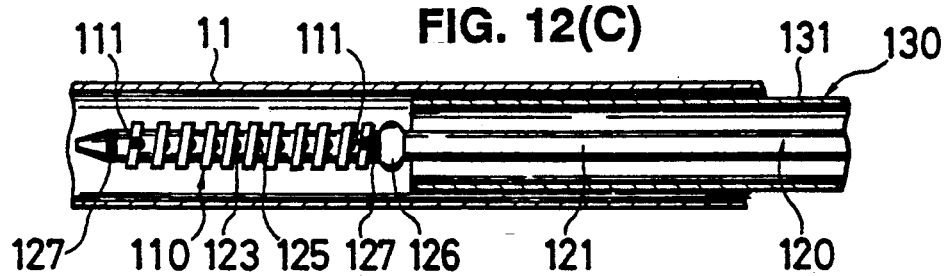
Figure 12D:
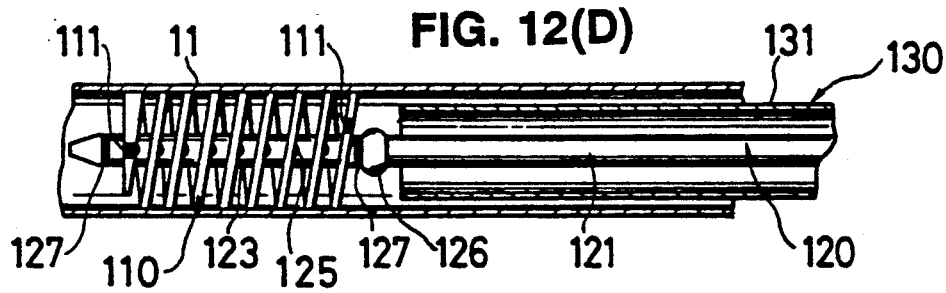
Figure 12E:
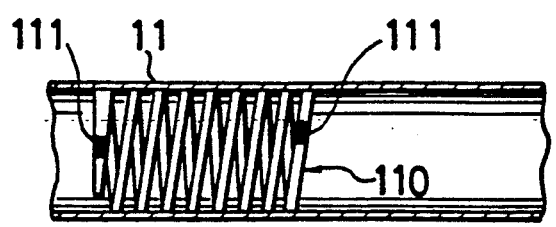

The stent 110 thus inserted into the desired location is projected out of the catheter sheath 130 (FIG. 12(C)), while it is wound around the catheter 120 (FIG. 12(B)) by the cooling water red from the catheter sheath 130 and/or the communication apertures 125 of the catheter 120. After the stent 110 is thus projected (FIG. 12(C)), the supply of the cooling water is stopped. The stent 110 is heated by body temperature, and is expanded (FIG. 12(D)) to indwell in the desired location of the tubular organ (FIG. 12(E)).

Further, for withdrawing the stent thus indwelt in the desired location, the guide wire is passed the location where the stent 110 is indwelt, and along the guide wire, the combination of the catheter 120 and the catheter sheath 130 is inserted into the location. The diatal end portion of the catheter 120 is then projected out of the catheter sheath 130. The stent 110 is reduced in size by the cooling water fed from the catheter sheath 130 and/or the communication apertures 125 of the catheter 120 and is wound around the catheter attaching portion of the catheter 120. The wound stent 110 can be withdrawn by being pulled into the catheter sheath 130 together with the catheter 120. In this case too, only a small amount of the cooling water is required. The stent 110 after being pulled into the catheter sheath 130 can be definitely withdrawn without being caught or deformed midway through.

In an embodiment according to this invention, when an expansion unit is formed by a unidirectional shape memory alloy, a coil-like or mesh-like, substantially cylindrical expansion unit is utilized. The unit memorizes outside diameter, equal to or somewhat larger than the inside diameter of a tubular organ where the unit is to rest at around body temperature.

Since the expansion unit can be changed freely in size at temperature (at or under the transformation point) substantially below body temperature, it is sheathed by the catheter sheath while it is wound around the a unit-attaching portion in the vicinity of the distal end portion of the catheter. The expansion unit is readily indwelt by inserting the combination of the expansion unit attached to the catheter and the sheath, into which the catheter is sheathed.

Namely, the guide wire is inserted by a known technique into the tubular organ where the expansion unit is to rest, and then, along the guide wire, the unit is readily inserted into the desired location by using the above combination. At this stage, in this invention, because of the catheter sheath, the expansion unit is not directly exposed to the tubular organ, and is prevented from being caught or deformed midway through.

After the expansion unit thus inserted into the desired location is projected out of the catheter sheath, while it is attached to the catheter, the unit is expanded in size by the heat of the body temperature so as to rest in the direction location of the tubular organ.

When the expansion unit, made of the above-described unidirectional shape memory alloy, is inserted, the cooling water may be fed from the catheter sheath, and when the unit is indwelt, warm water from the catheter sheath. Furthermore, in a preferred embodiment according to the present invention, the catheter can be provided with a passageway extending from its base to a location at least as far as the vicinity of the distal end portion and the communication apertures, through which the cooling and the warm water may be fed, for communicating the passageway with the surface of the unit-attaching portion in the vicinity of its distal end portion.

The effects of the embodiments according to this invention will now be specifically described.

EXAMPLE 1

A stent made of bidirectional shape memory alloy was indwelt and withdrawn, using the following materials.

The material of the stent was Ti-Ni binary alloy (approximately 51 percent Ni atoms), and the shape of the stent (wall thickness: $t=0.03$ mm, width: $w=1$ mm) was formed into a spiral, as shown in FIG. 2. The stent was changed in its diameter, to $\phi 1.6$ mm at or under 20° C., and to $\phi 2.8$ mm at or over 32° C. Two gold markers (wall thickness $t=0.02$ mm, $w=1.0$ mm) were fixed to the both ends of the stent.

The material of the catheter was a blend of polyethylene and EVA, and the shape of the catheter was as shown in FIG. 3.

The material composition of the catheter sheath was 100 parts by weight of polyvinyl chloride, 50 parts by weight of $Bi_2O_3$ and 26 parts by weight of diethylhexylphthalate, and the shape of the sheath (outside diameter 3.0 mm, inside diameter 2.6 mm and wall thichness 0.2 mm) was as shown in FIG. 4.

The stent was indwelt and withdrawn in accordance with the following procedures.

① 80 mg of aspirin and 50 mg of dipyridamole were orally administered to a mongrel dog (17 kg) one day prior to an operation and again on the day of the operation.

② Under general anesthesia, the dog was heparinized (200 U/kg) after an introducer was indwelt by a know technique in an arteria femoralis.

③ A replacing guide wire was inserted by a known technique into a chosen blood vessel. A right arteria cervicalis superficialis was chosen in this case.

④ The combination of the stent, the catheter and the sheath (Refer to FIG. 1) was inserted, along the guide wire, into a location just before the indwelling location.

⑤ 30 ml per minute of the cooling water (ice-cooled physiological salt solution) was fed from the catheter side pores (communication apertures) to contract the stent.

⑥ The catheter was pushed out of the sheath to move it to the location where the catheter was to be indwelt. The feeding of the cooling water was stopped to expand and indwell the stent, and then the catheter sheath was withdrawn.

⑦ Thirty minutes later, along the guide wire, the combination of the catheter and the sheath was inserted into a location just before the indwelling location and then the catheter alone was inserted farther into the indwelling location, followed by the feeding of the cooling water.

⑧ After it was confirmed that the stent was wound around the catheter, the catheter together with the stent was pulled into the sheath. The feeding of the cooling water was then stopped and the stent together with the sheath was pulled out of the dog's body, thus completing the withdrawal operation.

The above procedures, from ③ to ⑧, were performed by using X-ray transmission.

By the above-mentioned procedures, it has been proved that indwelling and withdrawing of the stent can be easily performed.

EXAMPLE 2

A stent made of the unidirectional shape memory alloy was easily indwelt by the following devices and procedures.

The stent had the same measurements and composition as the first embodiment. A 2.8 mm shape with a temperature at or over 42° C. was memorized.

The same catheter and catheter sheath as in the first example was used.

① In the same way as in the first example, the guide wire was indwelt in the right arteria cervical is superficialis of a mongrel dog, the above stent, together with the sheath, while the stent was wound around the catheter, being inserted into the indwelling location along the guide wire.

② The catheter and the stent were projected out at the indwelling location, and physiological salt solution heated up to 45° C. was injected from the catheter side pores. The stent was thus expanded and indwelt.

EXAMPLE 3

Before a stent, which had the same composition as the first example, with a spiral shape (wall thickness: $t=0.015$ mm, width: $w=1.0$ mm), as shown in FIG. 2, and a diameter changed to $\phi 1.4$ mm with a temperature at or under 20° C., and to $\phi 2.8$ mm with a temperature at or over 32° C., was inserted or withdrawn, a guiding catheter was indwelt. The above combination was guided by the guiding catheter.

The material of the guiding catheter was made of polyurethane, and the outside diameter of the catheter was $\phi$3.0 mm and the inside diameter $\phi$2.4 mm.

The material of the catheter sheath was the same as in the first embodiment, and the outside diameter of the sheath was $\phi$2.0 mm and the inside diameter $\phi$1.8 mm.

The material of the catheter was a blend of polyethylene and EVA, and the shape was as shown in FIG. 3.

The combination of the guiding catheter, the stent, the catheter and the catheter sheath was firmly guided by the guiding catheter to a point in the blood vessel which was midway to the desired location. The combination was directly inserted into the blood vessel after travelling through the end where the guiding catheter was indwelt. As a result, it was proved that the stent could be easily indwelt and withdrawn.

INDUSTRIAL APPLICABILITY

An expansion unit according to the present invention is utilized for maintaining the inside measurements of the lumen of such tubular organ as, for example, a blood vessel, a digestive tube or an air tube so as to prevent a coronary artery from relapsing into a constricted state after it has been dilated and indwelt by an angiectasia catheter.

An apparatus according to this invention is used for indwelling and withdrawing the aforementioned expansion unit.

We claim:

1. A tubular-organ expansion unit comprising:
    a mesh-like cylindrical body comprising a plurality of thin-woven wires that are formed of a shape memory alloy which is insertable into a tubular body organ and which is capable of maintaining an inside diameter of a lumen of the tubular body organ, said cylindrical body having a given X-ray contrast; and
    X-ray contrast enhancing means on at least a portion of said cylindrical body for improving the X-ray contrast of at least said portion of said cylindrical body relative to said given X-ray contrast.

2. A tubular-organ expansion unit according to claim 1, wherein the cylindrical body comprises a coil-like member.

3. A tubular-organ expansion unit according to claim 1, wherein said cylindrical body has a helical shape.

4. A tubular-organ expansion unit according to claim 1, wherein said cylindrical body has a longitudinal axis, and wherein said cylindrical body includes a slit formed substantially parallel to the longitudinal axis.

5. A tubular-organ expansion unit according to claim 1, wherein:
    the shape memory alloy has a given density; and
    the X-ray contrast enhancing means comprises a metal plated on said cylindrical body, said metal having a density higher then the given density of said shape memory alloy.

6. A tubular-organ expansion unit according to claim 1, wherein:
    the shape memory alloy has a given density; and
    said cylindrical body has a metal pressed thereon, said metal having a higher density than said given density of said shape memory alloy.

7. A tubular-organ expansion unit according to claim 1, wherein:
    the shape memory alloy has a given density; and
    said cylindrical body has a metal wound thereon having a higher density than said given density of said shape memory alloy.

8. A tubular-organ expansion apparatus for indwelling a tubular-organ expansion unit in a lumen of a tubular body organ, comprising:
    a tubular-organ expansion unit including a mesh-like substantially tubular body comprising a plurality of woven wires, said tubular body having a given radial dimension and an outside diameter when in an unexpanded state, said woven wires of said tubular body comprising a shape memory alloy having a given X-ray contrast, and said tubular body further being capable of changing the given radial dimension thereof in response to changes in temperature;
    a catheter including:
        a base portion having an outside diameter;
        a distal end portion having an outside diameter;
        an outside portion;
        a tubular-organ expansion unit attaching portion having a periphery in the vicinity of the distal end portion of said catheter for attaching the tubular-organ expansion unit to the catheter; and
        a catheter sheath having first and second open end portions for sheathing said tubular-organ expansion unit when said tubular-organ expansion unit is attached to said tubular-organ expansion unit attaching portion of said catheter; and
    X-ray contrast enhancing means formed on at least a portion of said tubular-organ expansion unit for improving the X-ray contrast of at least a portion of said shape metal alloy relative to said given X-ray contrast.

9. A tubular-organ expansion apparatus according to claim 8, wherein:
    said catheter is provided with a passageway extending from the base portion thereof to at least a position in the vicinity of the distal end portion thereof; and
    at least one of side pores and slit-like apertures formed in said catheter for providing communication with said tubular-organ expansion unit-attaching portion of the catheter positioned in the vicinity of the distal end portion of said catheter and providing fluid communication between said passageway and the outside portion of said catheter.

10. A tubular-organ expansion apparatus according to claim 9, wherein at least one of the outside diameter of the base portion of the catheter and the outside diameter of the distal end portion of said catheter are larger than the outside diameter of said tubular-organ expansion unit attached to said tubular-organ expansion unit-attaching portion of said catheter when said tubular-organ expansion unit is in an unexpanded state.

11. A tubular-organ expansion apparatus according to claim 9, wherein said catheter further comprises:
    a catheter lumen extending from the base portion of said catheter to at least a position of the catheter in the vicinity of the distal end portion thereof; and
    a hollow hub having a hub lumen therein provided on said base portion of said catheter for communicating with said catheter lumen; and
    said passageway being defined at least by said catheter lumen and said hub lumen.

12. A tubular-organ expansion apparatus according to claim 11, wherein said hollow hub comprises:

a branch hub having two ports; and
wherein a check valve is provided in one of said two ports.

13. A tubular-organ expansion apparatus according to claim 8, wherein said catheter is provided with at least one X-ray non-transmission marker in the vicinity of the distal end portion thereof.

14. A tubular-organ expansion apparatus according to claim 13, wherein said catheter sheath includes at least one of:
an X-ray non-transmission material, and said at least one X-ray non-transmission marker positioned in the vicinity of the distal end portion of the catheter.

15. A tubular-organ expansion apparatus according to claim 8, wherein said catheter sheath comprises:
a sheath lumen extending between the first and second open end portion thereof; and
a hollow hub including a hub lumen provided on the base portion of the catheter; and
a check valve positioned in the hollow hub for controlling fluid communicating between said sheath lumen and said hub lumen.

16. A tubular-organ expansion apparatus for indwelling a tubular-organ expansion unit in a lumen of a tubular body organ, comprising:
a tubular-organ expansion unit including a substantially mesh-like tubular body comprising a plurality of woven wires, said tubular body having a given radial dimension, and an outside diameter when in an unexpanded state, said woven wires of said tubular body comprising a bidirectional shape memory alloy which is capable of changing the given radial dimension thereof in response to a change in temperature;
a catheter including:
a base portion having an outside diameter;
a distal end portion having an outside diameter;
an outside portion having an outside diameter;
a tubular-organ expansion unit attaching portion having an outside diameter and a periphery in the vicinity of the distal end portion of said catheter for attaching the tubular-organ expansion unit to the catheter; and
a catheter sheath having first and second open end portions and having an inside diameter which is no larger than the outside diameter of the tubular-organ expansion unit, when said tubular-organ expansion unit is in the expanded state;
said catheter sheath sheathing said tubular-organ expansion unit when said tubular-organ expansion unit is attached to said tubular-organ expansion unit attaching portion of said catheter.

17. A tubular-organ expansion apparatus according to claim 16, wherein:
said catheter is provided with a passageway extending from the base portion thereof to at least a position in the vicinity of the distal end portion thereof; and
at least one of pores and slit-like apertures are formed in said catheter for providing communication with said tubular-organ expansion unit attaching portion of the catheter positioned in the vicinity of the distal end portion of said catheter and for providing fluid communication between said passageway and the outside portion of said catheter.

18. A tubular-organ expansion apparatus according to claim 17, wherein said catheter further comprises:
a catheter lumen extending from the base portion of the catheter to at least a position of the catheter in the vicinity of the distal end portion thereof;
a hollow hub having a hub lumen therein provided on said base portion of said catheter for communicating with said catheter lumen; and
said passageway being defined at least by said catheter lumen and said hub lumen.

19. A tubular-organ expansion apparatus according to claim 18, wherein said hollow hub further comprises:
a branch hub having two ports; and
a check valve provided in one of said two ports.

20. A tubular-organ expansion apparatus according to claim 16, wherein:
both said outside diameter of said catheter and the outside diameter of said tubular-organ expansion unit attaching portion of the catheter in the vicinity of the distal end portion of said catheter are substantially equal in diameter to each other; and
wherein both said outside diameters are at least equal in size to the inside diameter of the tubular-organ expansion unit when said tubular-organ expansion unit is in the unexpanded state so that said tubular-organ expansion unit attaching portion of the catheter is capable of having said tubular-organ expansion unit attached thereto at a temperature which is substantially below body temperature.

21. A tubular-organ expansion apparatus according to claim 16, wherein at least one of the outside diameter of the base portion of said catheter and the outside diameter of the distal end portion of said catheter are larger than the outside diameter of said tubular-organ expansion unit attached to said tubular-organ expansion unit attaching portion of said catheter when said tubular-organ expansion unit is in the unexpanded state.

22. A tubular-organ expansion apparatus according to claim 17, wherein said catheter is provided with at least one X-ray non-transmission marker in the vicinity of the distal end portion of said catheter.

23. A tubular-organ expansion apparatus according to claim 22, wherein said catheter sheath includes at least one of:
an X-ray non-transmission material; and
said at least one X-ray non-transmission marker positioned in the vicinity of the distal end portion of the catheter.

24. A tubular-organ expansion apparatus according to claim 16, wherein said catheter sheath comprises:
a sheath lumen extending between the first and second open end portions thereof; and
a hollow hub including a hub lumen provided on the base portion of the catheter; and
a check valve is positioned in the hollow hub for controlling fluid communicating between said sheath lumen and said hub lumen.

25. A method of medically treating a lumen of a tubular body organ, comprising:
indwelling a tubular-organ expansion unit having a given X-ray contrast into the lumen of the tubular body organ, said tubular-organ expansion unit being defined substantially by a shape memory alloy having a cylindrical tubular body, a diameter of said tubular body changing in size in response to a change in temperature;
attaching said tubular-organ expansion unit to a periphery of a unit-attaching portion of a catheter having a distal end portion, said unit attaching portion being positioned in the vicinity of the distal end portion of the catheter;

sheathing the thus attached tubular-organ expansion unit and catheter unit attaching portion in a catheter sheath having first and second open end portions;

then inserting the thus sheathed tubular organ expansion unit attached to the catheter into a desired location of the tubular organ, said catheter and said tubular-organ expansion unit being projectable out of said catheter sheath; and then expanding the tubular-organ expansion unit with heat of the body organ to thereby indwell said tubular-organ expansion unit into said desired location; and enhancing the X-ray contrast of at least a portion of said tubular-organ expansion unit relative for said given X-ray contrast of said tubular-organ expansion unit.

26. A method for medically treating a lumen of a tubular body organ, comprising:

indwelling a tubular-organ expansion unit into the lumen of the tubular-body organ, said tubular-organ expansion unit being defined substantially by a bidirectional shape memory alloy having a cylindrical tubular body, a diameter of said tubular body changing diametrically in size in response to a change in temperature;

attaching said tubular-organ expansion unit to a periphery of a unit-attaching portion of a catheter having a distal end portion, said unit attaching portion being positioned in the vicinity of the distal end portion of the catheter;

forming a sheath of the catheter to have an inside diameter which is no longer than an outside diameter of the tubular-organ expansion unit when said tubular-organ expansions unit is in an expanded state, said catheter sheath having first and second open end portions;

sheathing the thus attached tubular-organ expansion unit and the unit attaching portion in the catheter sheath;

then inserting the thus sheathed tubular-organ expansion unit attached to the catheter through a lumen of a guiding catheter previously indwelt in the tubular organ into a desired location of the tubular organ;

projecting said catheter and said tubular-organ expansion unit out of said catheter sheath; and then expanding the tubular-organ expansion unit with heat of the body organ to thereby indwell said tubular-organ expansion unit into said desired location.

27. A medical treatment method according to claim 26, further comprising:

inserting the sheathed tubular-body expansion unit into a location in the body organ where said tubular-organ expansion unit is to be indwelt;

shrinking the size of the tubular-organ expansion unit by feeding a cool fluid thereto from at least one of said catheter sheath and said catheter in order to shrink the tubular-body expansion unit around said unit-attaching portion of said catheter, said cool fluid being cooler than body temperature;

projecting said distal end portion of said catheter with the sheathed tubular-organ expansion unit shrunk therearound out of said catheter sheath; and subsequently drawing the tubular-organ expansion unit, together with said catheter, inside the catheter sheath.

28. A method of medically treating a lumen of a tubular body organ comprising:

indwelling a tubular-organ expansion unit having a given X-ray contrast into the lumen of the tubular-body organ, said tubular organ expansion unit being defined substantially by a shape memory alloy having a cylindrical tubular body, a diameter of said tubular body changing in size in response to a change in temperature;

attaching said tubular-organ expansion unit to a periphery of a unit-attaching portion of a catheter having a distal end portion, said unit attaching portion being positioned in the vicinity of the distal end portion of said catheter;

sheathing the thus attached tubular-organ expansion unit and catheter unit attaching portion in a catheter sheath having first and second open end portions;

then inserting the thus sheathed tubular-organ expansion unit attached to the catheter through a lumen of a guiding catheter previously indwelt in the tubular organ into a desired location of the tubular organ, said catheter and said tubular-organ expansion unit being projectable out of said catheter sheath;

expanding the tubular-organ expansion unit with heat of the body organ to thereby indwell said tubular-organ expansion unit into said desired location; and enhancing the X-ray contrast of at least a portion of said tubular-organ expansion unit relative to said given X-ray contrast of said tubular-organ expansion unit.

29. A method of medically treating a lumen of a tubular body organ comprising:

indwelling a tubular-organ expansion unit into the lumen of the tubular-body organ, said tubular-organ expansion unit being defined substantially by a bidirectional shape memory alloy having a cylindrical tubular body, a diameter of said tubular body changing in size in response to a change in temperature;

attaching said tubular-organ expansion unit to a periphery of a unit-attaching portion of a catheter having a distal end portion, said unit attaching portion being positioned in the vicinity of the distal end portion of the catheter;

forming a sheath for the catheter to have an inside diameter which is no larger than an outside diameter of the tubular-organ expansion unit when said tubular-organ expansion unit is in an expanded state;

said catheter sheath having first and second open end portions;

sheathing the thus attached tubular-organ expansion unit and catheter unit attaching portion in the catheter sheath;

then inserting the thus sheathed tubular organ expansion unit attached to the catheter into a desired location of the tubular organ, said catheter and said tubular-organ expansion unit being projectable out of said catheter sheath; and then expanding the tubular-organ expansion unit with heat of the body organ to thereby indwell said tubular-organ expansion unit into said desired location.

30. The medical treatment method according to claim 29, wherein:

after the combination of said catheter and said catheter sheath is inserted through the lumen of a guiding catheter previously indwelt in the tubular organ, into a location where said tubular-organ expansion unit is to be indwelt, the distal end portion of said catheter with the tubular-organ expansion unit attached thereto is projected out of said catheter sheath;

then reducing the size of said tubular-organ expansion unit by feeding a cool fluid from at least one of said catheter sheath and said catheter in order to shrink said tubular-organ expansion unit around the unit-attaching portion of said catheter, said cool fluid being cooler than body temperature; and then withdrawing said tubular-organ expansion unit, together with said catheter, inside the catheter sheath.

* * * * *

UNITED STATES PATENT AND TRADEMARK OFFICE
CERTIFICATE OF CORRECTION

PATENT NO. : 5,201,901
DATED : April 13, 1993
INVENTOR(S) : HARADA, Fumiaki

It is certified that error appears in the above-indentified patent and that said Letters Patent is hereby corrected as shown below:

Column 2, line 27, "turough" should be --through--.

Column 8, line 38, "th" should be --the--.

Column 11, line 11, "herical" should be --helical--.

Column 20, line 38 (claim 22), "claim 17" should be --claim 16--.

Signed and Sealed this

Twenty-fourth Day of May, 1994

Attest:

BRUCE LEHMAN

Attesting Officer     Commissioner of Patents and Trademarks